US012648899B2

(12) United States Patent
Arhamah

(10) Patent No.: US 12,648,899 B2
(45) Date of Patent: Jun. 9, 2026

(54) COSMETIC SALTS

(71) Applicant: TARA BRANDS EUROPE S.L.U., Badalona (ES)

(72) Inventor: Nawaf Arhamah, Badalona (ES)

(73) Assignee: TARA BRANDS EUROPE S.L.U., Badalona (ES)

( * ) Notice: Subject to any disclaimer, the term of this patent is extended or adjusted under 35 U.S.C. 154(b) by 517 days.

(21) Appl. No.: 18/271,621

(22) PCT Filed: Apr. 4, 2023

(86) PCT No.: PCT/EP2023/058848

§ 371 (c)(1),
(2) Date: Jul. 10, 2023

(87) PCT Pub. No.: WO2023/194382

PCT Pub. Date: Oct. 12, 2023

(65) Prior Publication Data

US 2024/0415754 A1 Dec. 19, 2024

(30) Foreign Application Priority Data

Apr. 4, 2022 (EP) .................................... 22382317

(51) Int. Cl.

| | |
|---|---|
| ***A61K 8/41*** | (2006.01) |
| ***A61Q 5/00*** | (2006.01) |
| ***C07C 211/09*** | (2006.01) |
| ***C07C 211/20*** | (2006.01) |

(52) U.S. Cl.

CPC ................ *A61K 8/41* (2013.01); *A61Q 5/002* (2013.01); *C07C 211/09* (2013.01); *C07C 211/20* (2013.01)

(58) Field of Classification Search

CPC ...... A61Q 5/002; C07C 211/09; C07C 211/20
See application file for complete search history.

(56) References Cited

U.S. PATENT DOCUMENTS

| | | | |
|---|---|---|---|
| 2015/0034117 | A1 | 2/2015 | Pressly et al. |
| 2018/0015015 | A1 | 1/2018 | Pressly et al. |

FOREIGN PATENT DOCUMENTS

| | | | |
|---|---|---|---|
| CN | 101264414 | A | 9/2008 |
| JP | 3-223846 | A | 10/1991 |
| WO | WO 2019/051441 | A1 | 3/2019 |

OTHER PUBLICATIONS

Ito, Y., et al., "Control of the Solid-State Photodimerization of Some Derivatives and Analogs of trans-Cinnamic Acid by Ethylenediamine," Tetarahedron Letters, Amsterdam, NL, Aug. 1, 1995, vol. 36, No. 34, pp. 6087-6090.

Joao, K., et al., "Poly(ionic liquid)s as phase splitting promoters in aqueous biphasic systems," Phys. Chem. Chem. Phys., Jan. 1, 2015, vol. 17, No. 41, pp. 27462-27472.

Pinkert A., et al., "Density, Viscosity and electrical conductivity of protic alkanolammonium ionic liquids," Phys. Chem. Chem. Phys., Jan. 1, 2011, vol. 13, No. 11, pp. 5136-5143.

EPO (Rijswijk, NL), English language version of the International Search Report, Form PCT/ISA/210, for International Application PCT/EP2023/058848, Jul. 14, 2023 (3 pages).

EPO (Rijswijk, NL), Written Opinion of the International Searching Authority, Form PCT/ISA/237, for International Application PCT/EP2023/058848, Jul. 14, 2023 (12 pages).

*Primary Examiner* — Andrew S Rosenthal

(74) *Attorney, Agent, or Firm* — Pauley Erickson & Swanson

(57) ABSTRACT

Disclosed herein is a salt of formula I:

$$[G]_g^q \qquad [A—L—E]^p \qquad \text{I}$$

wherein q is + or −; p is 2+, +, − or 2−; g is 1 or 2; G is selected from $R^5$—C≡C—$CO_2^-$; $R^5$—C≡C—C(═O)$S^-$, $R^5$—C≡C—$CS_2^-$, $R^5$—C≡C—$SO_2^-$, $R^5$—C≡C—S(═O)$S^-$, $R^5$—C≡C—$SO_3^-$, $R^5$—C≡C—S(═O)$_2S^-$, and a diallylammonium group, wherein $R^5$ is independently selected from H, linear or branched $C_{1-6}$ alkyl; L is straight-chain $C_{1-15}$ alkyl, wherein one or more $CH_2$ groups are independently replaced by —($CH_2$—O—$CH_2$)—, —($CH_2$—$CH_2$—O)—, —(O—$CH_2$—$CH_2$)—, C═O, —O—, ~S—, —NH— or —$NR^1$—, wherein $R^1$ is linear or branched $C_{1-6}$ alkyl; A is selected from $NR^2_3{}^+$, $CO_2^-$, C(═O)$S^-$, $CS_2^-$, $SO_2^-$, S(═O)$S^-$, $SO_3^-$ and S(═O)$_2S^-$, wherein $R^2$ is, for each occurrence independently, selected from H, linear or branched $C_{1-6}$ alkyl; E is selected from $NR^3_2$, $NR^3_3{}^+$, $CO_2H$, C(═O)SH, $CS_2H$, $SO_2H$, S(═O)SH, $SO_3H$, S(═O)$_2$SH, $CO_2^-$, C(═O)$S^-$, $CS_2^-$, $SO_2^-$, S(═O)$S^-$, $SO_3^-$, S(═O)$_2S^-$, wherein, for each occurrence independently, $R^3$ is selected from H, linear or branched $C_{1-6}$ alkyl; with the proviso that the overall charge of A and E is not 0 and with the proviso that the salt of formula I is overall neutral in charge.

17 Claims, No Drawings

COSMETIC SALTS

CROSS REFERENCE TO RELATED APPLICATION

This application is a National Phase filing in the United States, under 35 USC § 371, of PCT International Patent Application Number PCT/EP2023/058848, filed on 4 Apr. 2023 which claims the priority of European Patent Application Number EP 22382317.0, filed 4 Apr. 2022.

The above-referenced applications are hereby incorporated by reference herein in their entirety and are made a part hereof, including but not limited to those portions which specifically appear hereinafter.

BACKGROUND OF THE INVENTION

Field of the Invention

The present disclosure relates to salts and cosmetic preparations thereof and their use as hair care products. Further disclosed is a method for treatment of keratin materials, such as hair.

Discussion of Related Art

Human hair has a highly organized but complex structure. It is composed of the hair follicle, which is embedded in the skin, and hair shaft, which extends out of the skin. Hair is typically composed of two or three layers. The outermost layer is the cuticle, the middle layer is the cortex and in some cases there is a central medulla region that is made of packed cells and/or hollow spaces. A large part of the mass of the human hair is composed of fibrous structures called macrofibrils, each one consists of microfibrils held together by matrix proteins. Human hair consists of 65-95 wt % proteins, predominantly keratin which is a fibrous, helicoidal protein particularly rich in the amino acid cysteine, whose thiol groups may form disulfide crosslinks adding rigidity and resistance to the entire hair structure.

There are various treatments for hair, such as bleaching, dyeing, straightening and permanent waving, during which hair may become overprocessed or damaged due to the chemicals needed to effect the change desired. For example, some known hair straightening processes consist of treatment with alkaline straightener. The high pH (9.0-14.0) causes the hair to swell, which allows the alkaline agent to penetrate into the hair fibers, where it reacts with keratin and causes breaking and rearranging of the disulfide bridges present in keratin, allowing hair to be stretched. In addition to chemically caused damage, physical treatments such as frequent and/or high heat or environmental exposure may produce changes in hair texture and lead to further often permanent damage.

SUMMARY OF THE INVENTION

It would be highly desirable to be able to avoid, minimize, alleviate or repair any such damage that occurs during those hair treatment processes and in particular to restore disulfide bridges to regain and improve hair quality, strength and texture.

It is an object of the present disclosure to advance the state of the art of hair repair. It is a further object of the present disclosure to provide salts and preparations for use as hair care products, which are preferably able to crosslink thiol moieties. The thiol moieties to be crosslinked may, for example, have been formed by cleavage of disulfide bridges as a result of physical or chemical hair treatments. It is a further object of the present disclosure to enhance the restoration of disulfide bridges using the inventive linkers in hair.

Applicants have developed thiol-reactive crosslinking agents which are capable of crosslinking thiol moieties, thus emulating disulfide bridges. The thiol moieties to be crosslinked may, for example, result from prior cleavage of disulfide bridges, e.g. as a result of physical or chemical hair treatments. By crosslinking the thiol moieties, the thiol-reactive crosslinking agents disclosed herein effectively enable restoration of disulfide bridges.

The present disclosure is in a first aspect directed to salts of formula I $$[G]_g^q \qquad [A—L—E]^p \qquad \text{I}$$

wherein q is + or −;

p is 2+, +, − or 2−;

g is 1 or 2;

G is selected from $R^5—C≡C—CO_2^-$, $R^5—C≡C—C(=O)S^-$, $R^5—C≡C—CS_2^-$, $R^5—C≡C—SO_2^-$, $R^5—C≡C—S(=O)S^-$, $R^5—C≡C—SO_3^-$, $R^5—C≡C—S(=O)_2S^-$, and a diallylammonium group, wherein $R^5$ is independently selected from H, linear or branched $C_{1-6}$ alkyl;

L is straight-chain $C_{1-15}$ alkyl, wherein one or more $CH_2$ groups are independently replaced by $—(CH_2—O—CH_2)—$, $—(CH_2—CH_2—O)—$, $—(O—CH_2—CH_2)—$, $C=O$, $—O—$, $—S—$, $—NH—$ or $—NR^1—$, wherein $R^1$ is linear or branched $C_{1-6}$ alkyl;

A is selected from $NR^2{}_3^+$, $CO_2^-$, $C(=O)S^-$, $CS_2^-$, $SO_2^-$, $S(=O)S^-$, $SO_3^-$ and $S(=O)_2S^-$, wherein $R^2$ is, for each occurrence independently, selected from H, linear or branched $C_{1-6}$ alkyl;

E is selected from $NR^3{}_2$, $NR^3{}_3^+$, $CO_2H$, $C(=O)SH$, $CS_2H$, $SO_2H$, $S(=O)SH$, $SO_3H$, $S(=O)_2SH$, $CO_2^-$, $C(=O)S^-$, $CS_2^-$, $SO_2^-$, $S(=O)S^-$, $SO_3^-$, $S(=O)_2S^-$, wherein, for each occurrence independently, $R^3$ is selected from H, linear or branched $C_{1-6}$ alkyl;

with the proviso that the overall charge of A and E is not 0 and with the proviso that the salt of formula I is overall neutral in charge.

In some embodiments, the present disclosure is directed towards a salt of formula II

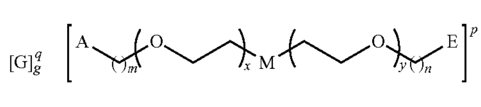

II wherein q is + or −;

p is 2+, +, − or 2−;

g is 1 or 2;

G is selected from $R^5—C≡C—CO_2^-$, $R^5—C≡C—C(=O)S^-$, $R^5—C≡C—CS_2^-$, $R^5—C≡C—SO_2^-$, $R^5—C≡C—S(=O)S^-$, $R^5—C≡C—SO_3^-$, $R^5—C≡C—S(=O)_2S^-$, and $(CH_2=CH—CH_2)_iNR^4{}_{(4-i)}^+$, wherein i is independently selected from 2 and 3, wherein $R^4$ is independently selected from H, linear or branched $C_{1-6}$ alkyl, wherein $R^5$ is independently selected from H, linear or branched $C_{1-6}$ alkyl;

A is selected from $NR^2_3{}^+$, $CO_2^-$, $C(=O)S^-$, $CS_2^-$, $SO_2^-$, $S(=O)S^-$, $SO_3^-$, $S(=O)_2S^-$, wherein $R^2$ is, for each occurrence independently, selected from H, linear or branched $C_{1-6}$ alkyl;

E is selected from $NR^3_2$, $NR^3_3{}^+$, $CO_2H$, $C(=O)SH$, $CS_2H$, $SO_2H$, $S(=O)SH$, $SO_3H$, $S(=O)_2SH$, $CO_2^-$, $C(=O)S^-$, $CS_2^-$, $SO_2^-$, $S(=O)S^-$, $SO_3^-$, $S(=O)_2S^-$, wherein, for each occurrence independently, $R^3$ is selected from H, linear or branched $C_{1-6}$ alkyl;

M is selected from O, S, NH and $NR^1$, wherein $R^1$ is linear or branched $C_{1-6}$ alkyl;

m and n are independently selected from 1, 2 and 3;

x and y are independently selected from 0, 1 and 2;

with the proviso that the overall charge of A and E is not 0 and with the proviso that the salt of formula I is overall neutral in charge.

In some embodiments of a salt of formula I or II, the diallylammonium group is a moiety of formula d1 or d2 d1

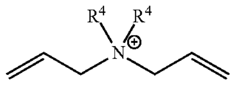

d2

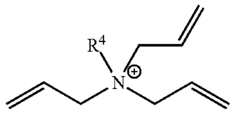

wherein, for each occurrence independently, $R^4$ is selected from H, linear or branched $C_{1-6}$ alkyl.

In some embodiments of a salt of formula I or II, G is selected from $R^5C{\equiv}C{-}CO_2^-$, $R^5C{\equiv}C{-}C(=O)S^-$, $R^5C{\equiv}C{-}CS_2^-$, $R^5C{\equiv}C{-}SO_2^-$, $R^5C{\equiv}C{-}S(=O)S^-$, $R^5C{\equiv}C{-}SO_3^-$, $R^5C{\equiv}C{-}S(=O)_2S^-$ and $(CH_2{=}CH_2CH_2)_iNR^4{}_r{}^+$, wherein i is selected from 2 and 3, r is selected such that the sum of i and r is 4, $R^5$ is, for each occurrence independently, selected from H, linear or branched $C_{1-6}$ alkyl, and $R^4$ is, for each occurrence independently, selected from H, linear or branched $C_{1-6}$ alkyl. In some embodiments of a salt of formula I or II, G is selected from $R^5C{\equiv}C{-}CO_2^-$ and $(CH_2{=}CH_2CH_2)_iNH_{(4-i)}{}^+$, wherein i is selected from 2 and 3, $R^5$ is selected from H, linear or branched $C_{1-6}$ alkyl. In some embodiments of a salt of formula I or II, G is selected from $HC{\equiv}C{-}CO_2^-$ and $(CH_2{=}CH_2CH_2)_2NH_2^+$.

In some embodiments, the present disclosure is directed towards a salt of formula III

III

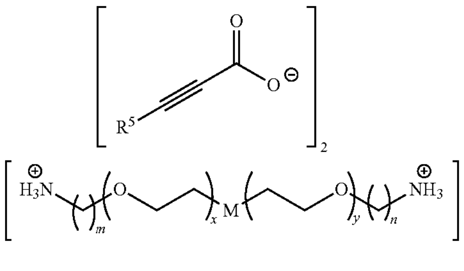

wherein

M is selected from O, S and $NR^6$, wherein $R^6$ is selected from H, linear or branched $C_{1-6}$ alkyl;

$R^5$ is, for each occurrence independently, selected from H, linear or branched $C_{1-6}$ alkyl;

m and n are independently selected from 1, 2 and 3;

x and y are independently selected from 0, 1 and 2.

In some embodiments of a salt of formula III, $R^5$ is H and M is O.

In some embodiments of a salt of formula III, m and n are independently selected from 2 or 3. In preferred embodiments of a salt of formula III, m and n are both selected from 2 or 3.

In some embodiments, the present disclosure is directed towards a salt of formula IV

IV

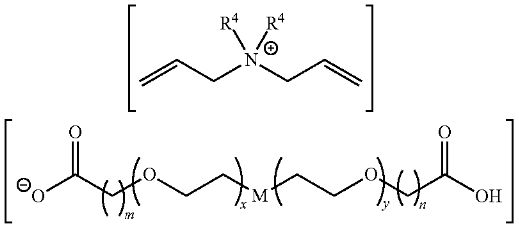

wherein

M is selected from O, S and $NR^6$, wherein $R^6$ is selected from H, linear or branched $C_{1-6}$ alkyl;

$R^4$ is, for each occurrence independently, selected from H, linear or branched $C_{1-6}$ alkyl;

m and n are independently selected from 1, 2 and 3;

x and y are independently selected from 0, 1 and 2.

In some embodiments of a salt of formula IV, $R^4$ is H and M is O.

In some embodiments of a salt of formula IV, m and n are independently selected from 1 and 2.

In some embodiments of a salt of formula II, III or IV, m is equal to n. In some embodiments of a salt of formula II, III or IV, m is equal to n and x is equal to y. In some embodiments of a salt of formula II, III or IV, m is equal to n and x is different from y.

In a second aspect, the disclosure is directed to a cosmetic preparation comprising at least one salt according to any of the embodiments described herein.

In some embodiments of the cosmetic preparation, the cosmetic preparation further comprises at least one cosmetic additive selected from the group consisting of surfactants, oil components, emulsifiers, pearlescent waxes, consistency-enhancing agents, thickeners, superfatting agents, stabilizers, polymers, silicone compounds, fats, waxes, lecithins, phospholipids, UV light protection factors, humectants, biogenic agents, antioxidants, deodorants, antiperspirants, antidandruff agents, film-forming agents, swelling agents, insect repellents, self-tanning agents, tyrosine inhibitors (depigmentation agents), hydrotropes, solubilizers, preservatives, perfumed oils and dyes, as well as mixtures thereof.

In some embodiments of the cosmetic preparation further comprises a carrier, preferably a carrier selected from water, C(2-6)-alcohols, C(1-10)polyols, as well as oil components.

In a third aspect, the disclosure is directed to a salt, a composition or a cosmetic preparation according to any of the embodiments described herein, for use as hair care products.

In a fourth aspect, the disclosure is directed to the use of salts according to any of the embodiments described herein, for the production of cosmetic preparations, preferably hair care products.

In a fifth aspect, the disclosure is directed to a method for treatment of keratin materials, such as hair, the method comprising applying to the keratin materials a salt or a cosmetic preparation according any of the embodiments described herein.

The salts and cosmetic preparations disclosed herein are suitable for cosmetic use, in particular for the protection of healthy hair or the amelioration of damaged hair.

DETAILED DESCRIPTION OF THE INVENTION

In the context of the present disclosure, restoration of disulfide bridges refers to a process by which two thiol moieties are linked together (it is understood that the term "disulfide bridges" refers to two thiol moieties being linked using the salts of the invention and not directly linked —S—S— bonds). The thiol moieties may, for example, be part of keratin protein. The process of linking the thiol moieties together may involve reaction of each thiol with an electrophilic moiety in the crosslinking agent. The thiol-reactive crosslinking agents disclosed herein typically react with two thiol moieties to form a crosslinking unit which links the two thiol moieties together.

Unless specified otherwise the following general definitions apply to all salts of the disclosure according to the description.

The term "salt of the disclosure" as used herein, refers to salts represented by formulae I-IV and any of the specific examples disclosed herein.

It is understood that "independently of each other" means that when a group is occurring more than one time in any salt, its definition on each occurrence is independent from any other occurrence.

It is further understood that a dashed line or a solid line without attachment, such as —$C_{1-4}$ alkyl, depicts the site of attachment of a residue (i.e. a partial formula).

It is further understood that the abbreviations "C" and "N" are representative for all possible degrees of saturation, which typically do not result in radicals, nitrenes or carbenes, i.e. N includes —NH—, —N= and

,

C includes —$CH_2$—, =CH— and

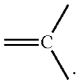

.

In addition, "C" as an atom in an aromatic or heteroaromatic ring which has a substituent $R^x$ at any suitable position, includes =CH— as well as =$CR^x$—. In addition, "C" as an atom in an aromatic or heteroaromatic ring which does not have substituents $R^x$ at any suitable position, includes =CH— and

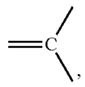

, as the case may be. It is understood and known to the skilled person that the general rules of valency must be abided by.

It is understood that whenever, in any formula, more than one $CH_2$ group of a straight-chain or branched alkyl chain, e.g. straight-chain or branched $C_{1-15}$ alkyl, is replaced by a heteroatom or a heteroatom-containing groups, the two or more $CH_2$ groups are replaced such that directly adjacent heteroatoms, e.g. —O—O— or —NH—NH—, are avoided. In particular, the two or more $CH_2$ groups shall be replaced such that the alkyl chain does not contain peroxide groups. The same holds true for the selection of generic groups defined herein, such as L, which are selected such that directly adjacent heteroatoms, e.g. —O—O— or —NH—NH—, are avoided.

The term "diallylammonium group" refers to a positively charged nitrogen atom that is covalently bonded to four substituents, wherein at least two of the four substituents are allyl substituents. Examples of a "diallylammonium group" include $(CH_2{=}CHCH_2)_2NR_2^+$, $(CH_2{=}CHCH_2)_3NR^+$, $(CH_2{=}CHCH_2)_4N^+$, $(CH_2{=}C(CH_3)CH_2)_2NR_2^+$, $(CH_2{=}C(CH_3)CH_2)_3NR^+$, $(CH_2{=}C(CH_3)CH_2)_4N^+$, $((CH_3)HC{=}CCH_2)_2NR_2^+$, $((CH_3)HC{=}CCH_2)_3NR^+$, $((CH_3)HC{=}CCH_2)_4N^+$, $((CH_3)_2C{=}CCH_2)_2NR_2^+$, $((CH_3)_2C{=}CCH_2)_3NR^+$, $((CH_3)_2C{=}CCH_2)_4N^+$, wherein R may independently be selected from H and linear or branched $C_{1-6}$ alkyl. In some embodiments, "diallylammonium group" refers to a positively charged nitrogen atom that is covalently bonded to four substituents, wherein two of the four substituents are allyl substituents and the other two substituents are not allyl substituents. In some embodiments, the "diallylammonium group" is $(CH_2{=}CHCH_2)_2NR_2^+$, wherein R may independently be selected from H and linear or branched $C_{1-6}$ alkyl. In some embodiments, the "diallylammonium group" is $(CH_2{=}CHCH_2)_2NH_2^+$.

Where E and Z isomers exists, such as in the crotyl fragment ($(CH_3)HC{=}CCH_2$—), the E-isomer, the Z-isomer and any mixture thereof are included.

"Allyl substituents" or "allyl" refers to a —$CH_2CH{=}CH_2$ unit that may optionally be substituted with one or more $C_{1-6}$ alkyl groups. Examples of "allyl" include —$CH_2CH{=}CH_2$, —$CH(CH_3)CH{=}CH_2$, —$C(CH_3)_2CH{=}CH_2$ unit —$CH_2C(Me){=}CH_2$, —$CH_2CH{=}CH(CH_3)$ (E and Z), —$CH_2CH{=}C(CH_3)_2$. In some embodiments, "allyl" is —$CH_2CH{=}CH_2$.

The terms "$C_{1-14}$ alkyl", "$C_{1-12}$ alkyl", "$C_{1-11}$ alkyl" and "$C_{1-6}$ alkyl" refer to a fully saturated branched or unbranched hydrocarbon moiety having the indicated number of carbon atoms. Representative examples of $C_{1-14}$ alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, iso-hexyl, neohexyl, heptyl, octyl, nonyl, decyl, dodecyl, etc. Representative examples of $C_{1-6}$ alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, iso-hexyl or neohexyl. One or more adjacent or non-adjacent $CH_2$ groups of $C_{1-14}$ alkyl, $C_{1-12}$ alkyl, $C_{1-11}$ alkyl and $C_{1-6}$ alkyl are independently replaced by one or more groups selected from —($CH_2$—O—$CH_2$)—, —($CH_2$—$CH_2$—O)—, and —(O—$CH_2$—$CH_2$)—, C=O, —O—, —S—, —NH—, —NR—, wherein R is linear or branched $C_{1-6}$ alkyl.

Certain parameters used herein, such as p and q, refer to charges. The charge may, for example, be 2+, +, − or 2−. 2+ refers to two positive charges, i.e. the respective ion is doubly positively charged. Conversely, 2− refers to two negative charges, i.e. the respective ion is doubly negatively charged. A charge typically refers to an ion, which may be an entire chemical moiety or fragment or entity. The charge of an ion refers to the overall charge of that ion, which may be calculated by adding all positive and negative charges comprised in the ion. As an example, an ion comprising an ammonium group and two carboxylate groups would have an overall charge of −. The charge of an ion may be delocalized over more than one atom. The charge may also be localized on a small number of atoms, such as one atom.

Based on the definitions given throughout the application the skilled person knows which combinations are synthetically feasible and realistic, e.g. typically combinations of groups leading to some heteroatoms directly linked to each other, e.g. —O—O—, are not contemplated, however synthetically feasible combinations, such as —S—N= in a isothiazole are contemplated.

In a first aspect, the disclosure is directed towards a salt of formula I $$[G]_g^q\ [A—L—E]^p \qquad \text{I}$$

wherein q is + o r−;

p is 2+, +, − or 2−;

g is 1 or 2;

G is selected from $R^5$—C≡C—$CO_2^-$, $R^5$—C≡C—C(=O)$S^-$, $R^5$—C≡C—$CS_2^-$, $R^5$—C≡C—$SO_2^-$, $R^5$—C≡C—S(=O)$S^-$, $R^5$—C≡C—$SO_3^-$, $R^5$—C≡C—$S(=O)_2S^-$, and a diallylammonium group, wherein $R^5$ is independently selected from H, linear or branched $C_{1-6}$ alkyl;

L is straight-chain $C_{1-15}$ alkyl, wherein one or more $CH_2$ groups are independently replaced by —($CH_2$—O—$CH_2$)—, —($CH_2$—$CH_2$—O)—, —(O—$CH_2$—$CH_2$)—, C=O, —O—, —S—, —NH— or —$NR^1$—, wherein $R^1$ is linear or branched $C_{1-6}$ alkyl;

A is selected from $NR^2_3{}^+$, $CO_2^-$, C(=O)$S^-$, $CS_2^-$, $SO_2^-$, S(=O)$S^-$, $SO_3^-$ and $S(=O)_2S^-$, wherein $R^2$ is, for each occurrence independently, selected from H, linear or branched $C_{1-6}$ alkyl;

E is selected from $NR^3_2$, $NR^3_3{}^+$, $CO_2H$, C(=O)SH, $CS_2H$, $SO_2H$, S(=O)SH, $SO_3H$, $S(=O)_2SH$, $CO_2^-$, C(=O)$S^-$, $CS_2^-$, $SO_2^-$, S(=O)$S^-$, $SO_3^-$, $S(=O)_2S^-$, wherein, for each occurrence independently, $R^3$ is selected from H, linear or branched $C_{1-6}$ alkyl;

with the proviso that the overall charge of A and E is not 0 and with the proviso that the salt of formula I is overall neutral in charge.

In some embodiments of a salt of formula I, q is +. In some embodiments of a salt of formula I, q is −.

In some embodiments of a salt of formula I, p is 2+. In some embodiments of a salt of formula I, p is +. In some embodiments of a salt of formula I, p is 2−. In some embodiments of a salt of formula I, p is −.

In some embodiments of a salt of formula I, g is 1. In some embodiments of a salt of formula I, g is 2.

In some embodiments of a salt of formula I, q is +, p is − and g is 1. In some embodiments of a salt of formula I, q is +, p is 2− and g is 2. In some embodiments of a salt of formula I, q is −, p is + and g is 1. In some embodiments of a salt of formula I, q is −, p is 2+ and g is 2.

In some embodiments of a salt of formula I, G is selected from $R^5$—C≡C—$CO_2^-$, $R^5$—C≡C—C(=O)$S^-$, $R^5$—C≡C—$CS_2^-$, and a diallylammonium group, wherein $R^5$ is independently selected from H, linear or branched $C_{1-6}$ alkyl. In some embodiments of a salt of formula I, G is selected from $R^5$—C≡C—$CO_2^-$, $R^5$—C≡C—C(=O)$S^-$, $R^5$—C≡C—$CS_2^-$ and $(CH_2{=}CH—CH_2)_iNR^4{}_{(4-i)}{}^+$, wherein i is independently selected from 2 and 3, wherein $R^4$ is independently selected from H, linear or branched $C_{1-6}$ alkyl, wherein $R^5$ is independently selected from H, linear or branched $C_{1-6}$ alkyl. In some embodiments of a salt of formula I, G is selected from $R^5$—C≡C—$CO_2^-$ and a diallylammonium group, wherein $R^5$ is independently selected from H, linear or branched $C_{1-6}$ alkyl. In some embodiments of a salt of formula I, G is selected from $R^5$—C≡C—$CO_2^-$ and $(CH_2{=}CH—CH_2)_iNR^4{}_{(4-i)}{}^+$, wherein i is independently selected from 2 and 3, wherein $R^4$ is independently selected from H, linear or branched $C_{1-6}$ alkyl, wherein $R^5$ is independently selected from H, linear or branched $C_{1-6}$ alkyl. In some embodiments of a salt of formula I, G is selected from H—C≡C—$CO_2$ and $(CH_2{=}CH—CH_2)_iNH_{(4-i)}{}^+$, wherein i is independently selected from 2 and 3.

In some embodiments of a salt of formula I, q is + and G is a diallylammonium group. In some embodiments of a salt of formula I, q is + and G is $(CH_2{=}CH—CH_2)_iNR^4{}_{(4-i)}{}^+$, wherein i is independently selected from 2 and 3, wherein $R^4$ is independently selected from H, linear or branched $C_{1-6}$ alkyl. In some embodiments of a salt of formula I, q is + and G is $(CH_2{=}CH—CH_2)_iNH_{(4-i)}{}^+$, wherein i is independently selected from 2 and 3. In the embodiments described in this paragraph, preferably, p is − and g is 1.

In some embodiments of a salt of formula I, q is − and G is selected from $R^5$—C≡C—$CO_2^-$, $R^5$—C≡C—C(=O)$S^-$, $R^5$—C≡C—$CS_2^-$, $R^5$—C≡C—$SO_2^-$, $R^5$—C≡C—S(=O)$S^-$, $R^5$—C≡C—$SO_3^-$, $R^5$—C≡C—$S(=O)_2S^-$, wherein $R^5$ is independently selected from H, linear or branched $C_{1-6}$ alkyl. In some embodiments of a salt of formula I, q is − and G is selected from $R^5$—C≡C—$CO_2^-$, $R^5$—C≡C—C(=O)$S^-$, $R^5$—C≡C—$CS_2^-$, wherein $R^5$ is independently selected from H, linear or branched $C_{1-6}$ alkyl. In some embodiments of a salt of formula I, q is − and G is $R^5$—C≡C—$CO_2^-$, wherein $R^5$ is independently selected from H, linear or branched $C_{1-6}$ alkyl. In the embodiments described in this paragraph, preferably, p is 2+ and g is 2.

In some embodiments of a salt of formula I, L is straight-chain $C_{1-10}$ alkyl, wherein one or more $CH_2$ groups are independently replaced by —($CH_2$—O—$CH_2$)—, —($CH_2$—$CH_2$—O)—, —(O—$CH_2$—$CH_2$)—, C=O, —O—, —S—, —NH— or —$NR^1$—, wherein $R^1$ is linear or branched $C_{1-6}$ alkyl. In some embodiments of a salt of formula I, L is straight-chain $C_{1-10}$ alkyl, wherein one or more $CH_2$ groups are independently replaced by —($CH_2$—O—$CH_2$)—, —($CH_2$—$CH_2$—O)—, —(O—$CH_2$—$CH_2$)—, C=O, —O— or —S—. In some embodiments of a salt of formula I, L is straight-chain $C_{1-10}$ alkyl, wherein one or more $CH_2$ groups are independently replaced by —($CH_2$—O—$CH_2$)—, —($CH_2$—$CH_2$—O)—, —(O—$CH_2$—$CH_2$)— or —O—.

In some embodiments of a salt of formula I, A is selected from $NR^2_3{}^+$, $CO_2^-$, C(=O)$S^-$, $CS_2^-$, wherein $R^2$ is, for each occurrence independently, selected from H, linear or branched $C_{1-6}$ alkyl. In some embodiments of a salt of formula I, p is + or 2+ and A is $NR^2_3{}^+$, wherein $R^2$ is, for each occurrence independently, selected from H, linear or branched $C_{1-6}$ alkyl. In some embodiments of a salt of formula I, p is − or 2− and A is $CO_2$, C(═O)$S^-$, $CS_2^-$, $SO_2^-$, S(═O)$S^-$, $SO_3^-$ and S(═O)$_2S^-$, wherein $R^2$ is, for each occurrence independently, selected from H, linear or branched $C_{1-6}$ alkyl. In some embodiments of a salt of formula I, p is − or 2− and A is selected from $CO_2^-$, C(═O)$S^-$, $CS_2^-$. In some embodiments of a salt of formula I, p is − or 2− and A is $CO_2$.

In some embodiments of a salt of formula I, E is selected from $NR^3_2$, $NR^3_3{}^+$, $CO_2H$, C(═O)SH, $CS_2H$, $CO_2^-$, C(═O)$S^-$, $CS_2^-$, wherein, for each occurrence independently, $R^3$ is selected from H, linear or branched $C_{1-6}$ alkyl. In some embodiments of a salt of formula I, E is selected from $NR^3_2$, $NR^3_3{}^+$, $CO_2H$, $CO_2^-$, wherein, for each occurrence independently, $R^3$ is selected from H, linear or branched $C_{1-6}$ alkyl.

In some embodiments of a salt of formula I, q is +;

p is − or 2−;

g is 1 or 2;

G is a diallylammonium group;

L is straight-chain $C_{1-15}$ alkyl, wherein one or more $CH_2$ groups are independently replaced by —($CH_2$—O—$CH_2$)—, —($CH_2$—$CH_2$—O)—, —(O—$CH_2$—$CH_2$)—, C═O, —O—, —S—, —NH— or —$NR^1$—, wherein $R^1$ is linear or branched $C_{1-6}$ alkyl;

A is selected from $CO_2^-$, C(═O)$S^-$, $CS_2^-$, $SO_2^-$, S(═O)$S^-$, $SO_3^-$ and S(═O)$_2S^-$;

E is selected from $NR^3_2$, $CO_2H$, C(═O)SH, $CS_2H$, $SO_2H$, S(═O)SH, $SO_3H$, S(═O)$_2$SH, $CO_2^-$, C(═O)$S^-$, $CS_2^-$, $SO_2^-$, S(═O)$S^-$, $SO_3^-$, S(═O)$_2S^-$, wherein, for each occurrence independently, $R^3$ is selected from H, linear or branched $C_{1-6}$ alkyl;

with the proviso that the overall charge of A and E is not 0 and with the proviso that the salt of formula I is overall neutral in charge.

In some embodiments of a salt of formula I, q is −;

p is 2+ or +;

g is 1 or 2;

G is selected from $R^5$—C≡C—$CO_2^-$, $R^5$—C≡C—C(═O)$S^-$, $R^5$—C≡C—$CS_2^-$, $R^5$—C≡C—$SO_2^-$, R—C≡C—S(═O)$S^-$, R—C≡C—$SO_3^-$, $R^5$—C≡C—S(═O)$_2S^-$, wherein $R^5$ is independently selected from H, linear or branched $C_{1-6}$ alkyl;

L is straight-chain $C_{1-15}$ alkyl, wherein one or more $CH_2$ groups are independently replaced by —($CH_2$—O—$CH_2$)—, —($CH_2$—$CH_2$—O)—, —(O—$CH_2$—$CH_2$)—, C═O, —O—, —S—, —NH— or —$NR^1$—, wherein $R^1$ is linear or branched $C_{1-6}$ alkyl;

A is $NR^2_3{}^+$, wherein $R^2$ is, for each occurrence independently, selected from H, linear or branched $C_{1-6}$ alkyl;

E is selected from $NR^3_2$, $NR^3_3{}^+$, $CO_2H$, C(═O)SH, $CS_2H$, $SO_2H$, S(═O)SH, $SO_3H$, S(═O)$_2$SH, wherein, for each occurrence independently, $R^3$ is selected from H, linear or branched $C_{1-6}$ alkyl;

with the proviso that the overall charge of A and E is not 0 and with the proviso that the salt of formula I is overall neutral in charge.

In some embodiments, the salt of the invention is of formula II

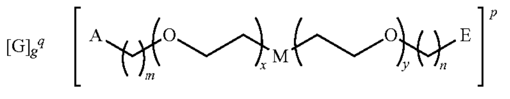

II wherein q is + or −;

p is 2+, − or 2−;

g is 1 or 2;

G is selected from $R^5$—C≡C—$CO_2^-$, $R^5$—C≡C—C(═O)$S^-$, $R^5$—C≡C—$CS_2^-$, $R^5$—C≡C—$SO_2^-$, $R^5$—C≡C—S(═O)$S^-$, $R^5$—C≡C—$SO_3^-$, $R^5$—C≡C—S(═O)$_2S^-$, and ($CH_2$═CH—$CH_2$)$_i$$NR^4_{(4-i)}{}^+$, wherein i is independently selected from 2 and 3, wherein $R^4$ is independently selected from H, linear or branched $C_{1-6}$ alkyl, wherein $R^5$ is independently selected from H, linear or branched $C_{1-6}$ alkyl;

A is selected from $NR^2_3{}^+$, $CO_2^-$, C(═O)$S^-$, $CS_2^-$, $SO_2^-$, S(═O)$S^-$, $SO_3^-$, S(═O)$_2S^-$, wherein $R^2$ is, for each occurrence independently, selected from H, linear or branched $C_{1-6}$ alkyl;

E is selected from $NR^3_2$, $NR^3_3{}^+$, $CO_2H$, C(═O)SH, $CS_2H$, $SO_2H$, S(═O)SH, $SO_3H$, S(═O)$_2$SH, $CO_2^-$, C(═O)$S^-$, $CS_2^-$, $SO_2^-$, S(═O)$S^-$, $SO_3^-$, S(═O)$_2S^-$, wherein, for each occurrence independently, $R^3$ is selected from H, linear or branched $C_{1-6}$ alkyl;

M is selected from O, S, NH and $NR^1$, wherein $R^1$ is linear or branched $C_{1-6}$ alkyl;

m and n are independently selected from 1, 2 and 3;

x and y are independently selected from 0, 1 and 2;

with the proviso that the overall charge of A and E is not 0 and with the proviso that the salt of formula II is overall neutral in charge.

In some embodiments of a salt of formula II, q is +. In some embodiments of a salt of formula II, q is −.

In some embodiments of a salt of formula II, p is 2+. In some embodiments of a salt of formula II, p is +. In some embodiments of a salt of formula II, p is 2−. In some embodiments of a salt of formula II, p is −.

In some embodiments of a salt of formula II, g is 1. In some embodiments of a salt of formula II, g is 2.

In some embodiments of a salt of formula II, q is +, p is − and g is 1. In some embodiments of a salt of formula II, q is +, p is 2− and g is 2. In some embodiments of a salt of formula II, q is −, p is + and g is 1. In some embodiments of a salt of formula II, q is −, p is 2+ and g is 2.

In some embodiments of a salt of formula II, G is selected from $R^5$—C≡C—$CO_2^-$, $R^5$—C≡C—C(═O)$S^-$, $R^5$—C≡C—$CS_2^-$, and ($CH_2$═CH—$CH_2$)$_i$$NR^4_{(4-i)}{}^+$, wherein i is independently selected from 2 and 3, wherein $R^4$ is independently selected from H, linear or branched $C_{1-6}$ alkyl, wherein $R^5$ is independently selected from H, linear or branched $C_{1-6}$ alkyl. In some embodiments of a salt of formula II, G is selected from $R^5$—C≡C—$CO_2^-$ and ($CH_2$═CH—$CH_2$)$_i$$NR^4_{(4-i)}{}^+$, wherein i is independently selected from 2 and 3, wherein $R^4$ is independently selected from H, linear or branched $C_{1-6}$ alkyl, wherein $R^5$ is independently selected from H, linear or branched $C_{1-6}$ alkyl. In some embodiments of a salt of formula II, G is selected from $R^5$—C≡C—$CO_2^-$ and ($CH_2$═CH—$CH_2$)$_i$$NH_{(4-i)}{}^+$, wherein i is independently selected from 2 and 3, wherein $R^5$ is independently selected from H, linear or branched $C_{1-6}$ alkyl.

In some embodiments of a salt of formula II, q is + and G is ($CH_2$═CH—$CH_2$)$_i$$NR^4_{(4-i)}{}^+$, wherein i is independently selected from 2 and 3, wherein $R^4$ is independently selected from H, linear or branched $C_{1-6}$ alkyl. In some embodiments of a salt of formula II, q is + and G is ($CH_2$═CH—$CH_2$)$_i$$NH_{(4-i)}{}^+$, wherein i is independently selected from 2 and 3. In the embodiments described in this paragraph, preferably, p is − and g is 1.

In some embodiments of a salt of formula II, q is − and G is selected from $R^5$—C≡C—$CO_2^-$, $R^5$—C≡C—C(═O)$S^-$, $R^5$—C≡C—$CS_2^-$, $R^5$—C≡C—$SO_2^-$, $R^5$—C≡C—S(═O)$S^-$, $R^5$—C≡C—$SO_3^-$, $R^5$—C≡C—S(═O)$_2$$S^-$, wherein $R^5$ is independently selected from H, linear or branched $C_{1-6}$ alkyl. In some embodiments of a salt of formula II, q is − and G is selected from $R^5$—C≡C—$CO_2^-$, $R^5$—C≡C—C(═O)$S^-$, $R^5$—C≡C—$CS_2^-$, wherein $R^5$ is independently selected from H, linear or branched $C_{1-6}$ alkyl. In some embodiments of a salt of formula II, q is − and G is $R^5$—C≡C—$CO_2^-$, wherein $R^5$ is independently selected from H, linear or branched $C_{1-6}$ alkyl. In the embodiments described in this paragraph, preferably, p is 2+ and g is 2.

In some embodiments of a salt of formula II, m and n are both selected from 1, 2 and 3. In some embodiments of a salt of formula II, m and n are 1. In some embodiments of a salt of formula II, m and n are 2. In some embodiments of a salt of formula II, m and n are 3.

In some embodiments of a salt of formula II, x and y are both selected from 0, 1 and 2. In some embodiments of a salt of formula II, x and y are both 0. In some embodiments of a salt of formula II, x and y are both 1. In some embodiments of a salt of formula II, x and y are both 2. In some embodiments of a salt of formula II, x is 0 and y is 1.

In some embodiments of a salt of formula II, A is selected from $NR^2_3{}^+$, $CO_2^-$, C(═O)$S^-$, $CS_2^-$, wherein $R^2$ is, for each occurrence independently, selected from H, linear or branched $C_{1-6}$ alkyl. In some embodiments of a salt of formula II, p is + or 2+ and A is $NR^2_3{}^+$, wherein $R^2$ is, for each occurrence independently, selected from H, linear or branched $C_{1-6}$ alkyl. In some embodiments of a salt of formula II, p is − or 2− and A is $CO_2$, C(═O)$S^-$, $CS_2$, $SO_2^-$, S(═O)$S^-$, $SO_3^-$ and S(═O)$_2$$S^-$, wherein $R^2$ is, for each occurrence independently, selected from H, linear or branched $C_{1-6}$ alkyl. In some embodiments of a salt of formula II, p is − or 2− and A is selected from $CO_2^-$, C(═O)$S^-$, $CS_2^-$. In some embodiments of a salt of formula II, p is − or 2− and A is $CO_2^-$.

In some embodiments of a salt of formula II, E is selected from $NR^3_2$, $NR^3_3{}^+$, $CO_2H$, C(═O)SH, $CS_2H$, $CO_2^-$, C(═O)$S^-$, $CS_2^-$, wherein, for each occurrence independently, $R^3$ is selected from H, linear or branched $C_{1-6}$ alkyl. In some embodiments of a salt of formula II, E is selected from $NR^3_2$, $NR^3_3{}^+$, $CO_2H$, $CO_2^-$, wherein, for each occurrence independently, $R^3$ is selected from H, linear or branched $C_{1-6}$ alkyl.

In some embodiments of a salt of formula II,
- q is +;
- p is − or 2−;
- g is 1 or 2;
- G is $(CH_2{=}CH{-}CH_2)_iNR^4_{(4-i)}{}^+$, wherein i is independently selected from 2 and 3, wherein $R^4$ is independently selected from H, linear or branched $C_{1-6}$ alkyl;
- A is selected from $CO_2^-$, C(═O)$S^-$, $CS_2^-$, $SO_2^-$, S(═O)$S^-$, $SO_3^-$, S(═O)$_2$$S^-$, wherein $R^2$ is, for each occurrence independently, selected from H, linear or branched $C_{1-6}$ alkyl;
- E is selected from $NR^3_2$, $CO_2H$, C(═O)SH, $CS_2H$, $SO_2H$, S(═O)SH, $SO_3H$, S(═O)$_2$SH, $CO_2^-$, C(═O)$S^-$, $CS_2^-$, $SO_2^-$, S(═O)$S^-$, $SO_3^-$, S(═O)$_2$$S^-$, wherein, for each occurrence independently, $R^3$ is selected from H, linear or branched $C_{1-6}$ alkyl;
- M is selected from O, S, NH and $NR^1$, wherein $R^1$ is linear or branched $C_{1-6}$ alkyl;
- m and n are independently selected from 1, 2 and 3;
- x and y are independently selected from 0, 1 and 2;
- with the proviso that the overall charge of A and E is not 0 and with the proviso that the salt of formula II is overall neutral in charge.

In some embodiments of a salt of formula II,
- q is −;
- p is 2+ or +;
- g is 1 or 2;
- G is selected from $R^5$—C≡C—$CO_2^-$, $R^5$—CC—C(═O)$S^-$, $R^5$—C≡C—$CS_2^-$, $R^5$—C≡C—$SO_2^-$, $R^5$—C≡C—S(═O)$S^-$, R—C≡C—$SO_3^-$, R—C≡C—S(═O)$_2$$S^-$, wherein $R^5$ is independently selected from H, linear or branched $C_{1-6}$ alkyl;
- A is $NR^2_3{}^+$, wherein $R^2$ is, for each occurrence independently, selected from H, linear or branched $C_{1-6}$ alkyl;
- E is selected from $NR^3_2$, $NR^3_3{}^+$, $CO_2H$, C(═O)SH, $CS_2H$, $SO_2H$, S(═O)SH, $SO_3H$, S(═O)$_2$SH, wherein, for each occurrence independently, $R^3$ is selected from H, linear or branched $C_{1-6}$ alkyl;
- M is selected from O, S, NH and $NR^1$, wherein $R^1$ is linear or branched $C_{1-6}$ alkyl;
- m and n are independently selected from 1, 2 and 3;
- x and y are independently selected from 0, 1 and 2;
- with the proviso that the overall charge of A and E is not 0 and with the proviso that the salt of formula II is overall neutral in charge.

In some embodiments of any of the salts disclosed herein, the diallylammonium group is a moiety of formula d1 or d2 d1

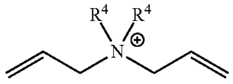

d2

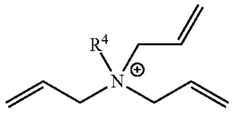

wherein, for each occurrence independently, $R^4$ is selected from H, linear or branched $C_{1-6}$ alkyl.

In some embodiments of any of the salts disclosed herein, the diallylammonium group is of formula d1 or d2, wherein $R^4$ is H.

In some embodiments of any of the salts disclosed herein, the diallylammonium group is a moiety of formula d1. In some embodiments of any of the salts disclosed herein, the diallylammonium group is a moiety of formula d2.

In some embodiments of the salts disclosed herein, the ion containing a diallylammonium group is $(CH_2{=}CHCH_2)_2NH_2$+.

In some embodiments, the salt of the invention is of formula III

III

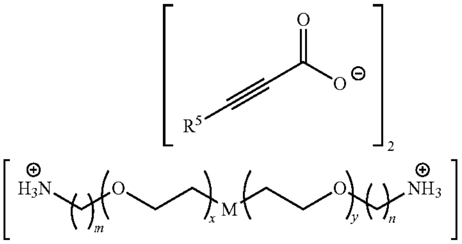

wherein

M is selected from O, S and $NR^6$, wherein $R^6$ is selected from H, linear or branched $C_{1-6}$ alkyl;

$R^5$ is, for each occurrence independently, selected from H, linear or branched $C_{1-6}$ alkyl;

m and n are independently selected from 1, 2 and 3;

x and y are independently selected from 0, 1 and 2.

In some embodiments of a salt of formula III, M is O. In some embodiments of a salt of formula III, M is S. In some embodiments of a salt of formula III, M is $NR^6$, wherein $R^6$ is selected from H, linear or branched $C_{1-6}$ alkyl.

In some embodiments of a salt of formula III, $R^5$ is H. In some embodiments of a salt of formula III, $R^5$ linear or branched $C_{1-6}$ alkyl.

In some embodiments of a salt of formula III, x and y are independently selected from 0 and 1. In some embodiments of a salt of formula III, x and y are selected from 0, 1 and 2. In some embodiments of a salt of formula III, x and y are selected from 0 and 1. In some embodiments of a salt of formula III, x and y are 0. In some embodiments of a salt of formula III, x and y are 1. In some embodiments of a salt of formula III, x is 0 and y is 1.

In some embodiments of a salt of formula III, m and n are independently selected from 2 and 3. In some embodiments of a salt of formula III, m and n are selected from 1, 2 and 3. In some embodiments of a salt of formula III, m and n are selected from 2 and 3. In some embodiments of a salt of formula III, m and n are 2. In some embodiments of a salt of formula III, m and n are 3.

In some embodiments of a salt of formula III, m and n are 2 and x and y are 0. In some embodiments of a salt of formula III, m and n are 3 and x and y are 1. In some embodiments of a salt of formula III, m and n are 2, x is 0 and y is 1. In some embodiments of a salt of formula III, m and n are 3, x is 0 and y is 1.

In some embodiments of a salt of formula III, M is O, m and n are 2 and x and y are 0. In some embodiments of a salt of formula III, M is O, m and n are 3 and x and y are 1. In some embodiments of a salt of formula III, M is O, m and n are 2, x is 0 and y is 1. In some embodiments of a salt of formula III, M is O, m and n are 3, x is 0 and y is 1.

In some embodiments, the salt of the invention is of formula IV

IV

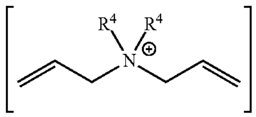

-continued

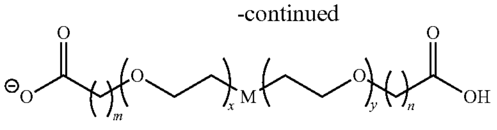

wherein

M is selected from O, S and $NR^6$, wherein $R^6$ is selected from H, linear or branched $C_{1-6}$ alkyl;

$R^4$ is, for each occurrence independently, selected from H, linear or branched $C_{1-6}$ alkyl;

m and n are independently selected from 1, 2 and 3;

x and y are independently selected from 0, 1 and 2.

In some embodiments of a salt of formula III, M is O. In some embodiments of a salt of formula III, M is S. In some embodiments of a salt of formula III, M is $NR^6$, wherein $R^6$ is selected from H, linear or branched $C_{1-6}$ alkyl.

In some embodiments of a salt of formula III, $R^4$ is H for each occurrence. In some embodiments of a salt of formula III, R linear or branched $C_{1-6}$ alkyl for each occurrence, such as methyl, ethyl or n-propyl, particularly methyl.

In some embodiments of a salt of formula IV, m and n are independently selected from 1 and 2. In some embodiments of a salt of formula IV, m and n are selected from 1, 2 and 3. In some embodiments of a salt of formula IV, m and n are selected from 1 and 2. In some embodiments of a salt of formula IV, m and n are 1. In some embodiments of a salt of formula IV, m and n are 2.

In some embodiments of a salt of formula IV, x and y are independently selected from 0 and 1. In some embodiments of a salt of formula IV, x and y are selected from 0, 1 and 2. In some embodiments of a salt of formula IV, x and y are selected from 0 and 1. In some embodiments of a salt of formula IV, x and y are 0. In some embodiments of a salt of formula IV, x and y are 1. In some embodiments of a salt of formula IV, x is 0 and y is 1.

In some embodiments of a salt of formula IV, m and n are 1 and x and y are 1. In some embodiments of a salt of formula IV, m and n are 1 and x and y are 0. In some embodiments of a salt of formula IV, m and n are 2 and x and y are 1.

In some embodiments of a salt of formula IV, M is O, m and n are 1 and x and y are 1. In some embodiments of a salt of formula IV, M is O, m and n are 1 and x and y are 0. In some embodiments of a salt of formula IV, M is O, m and n are 2 and x and y are 1.

In further specific embodiments, the disclosure is directed to the specific examples disclosed in Table 1.

TABLE 1

| | |
|---|---|
| SPC-TB-0015 | 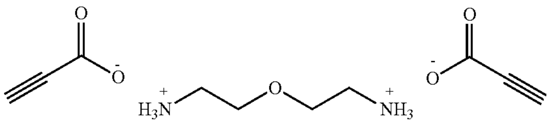 |
| SPC-TB-0016 | 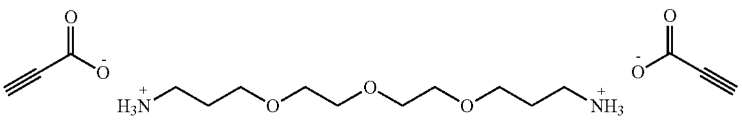 |

TABLE 1-continued

| | |
|---|---|
| SPC-TB-0017 | 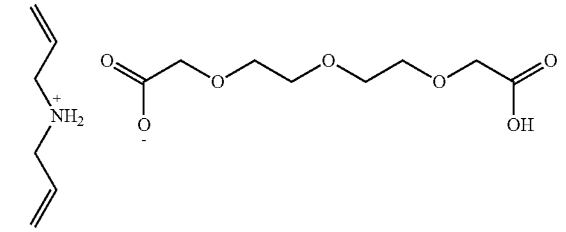 |
| SPC-TB-0018 | 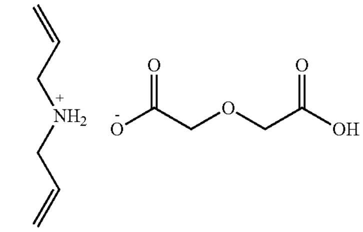 |
| SPC-TB-0019 | 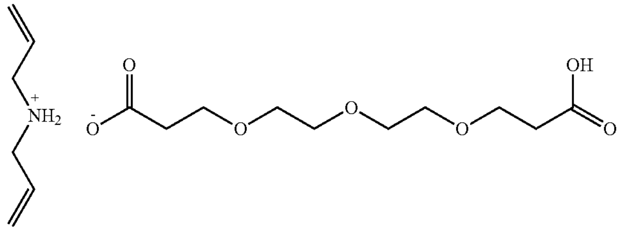 |
| SPC-TB-0020 | 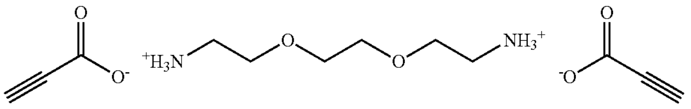 |

The salts of the disclosure may contain one or more asymmetric centers in the molecule. A salt without designation of the stereochemistry is to be understood to include all the optical isomers (e.g., diastereomers, enantiomers, etc.) in pure or substantially pure form, as well as mixtures thereof (e.g. a racemic mixture, or an enantiomerically enriched mixture). It is well known in the art how to prepare such optically active forms (e.g. by resolution of the racemic form by recrystallization techniques, by synthesis from optically-active starting materials, by chiral synthesis, by chromatographic separation using a chiral stationary phase, and other methods).

The salts may be isotopically-labeled compounds, for example, compounds including various isotopes of hydrogen, carbon, nitrogen, oxygen. The disclosed salts may exist in tautomeric forms and mixtures and separate individual tautomers are contemplated. In addition, some salts may exhibit polymorphism.

The salts of the disclosure may exist in solid, i.e. crystalline (e.g., polymorphs, i.e., different crystalline structures that have the same chemical composition but differ in packing, geometrical arrangement) or noncrystalline form (optionally as solvates) or liquid form. In the solid state, it may exist in, or as a mixture thereof. In crystalline solvates, solvent molecules are incorporated into the crystalline lattice during crystallization. The formation of solvates may include non-aqueous solvents such as, but not limited to, ethanol, isopropanol, DMSO, acetic acid, ethanolamine, or ethyl acetate, or aqueous solvents such as water (also called "hydrates"). Different polymorphs may be produced, for example, by changing or adjusting the reaction conditions or reagents.

In a further aspect, the disclosure also provides methods of preparation of the salts of formula I-IV of the disclosure.

In yet another aspect, the disclosure further provides a cosmetic preparation comprising an effective amount of one or more of the salts of the disclosure and one or more pharmaceutically acceptable carriers and/or excipients (also referred to as diluents). The excipients are acceptable in the sense of being compatible with the other ingredients of the formulation and not deleterious to the recipient thereof. The term "effective amount" as used herein refers to the amount of a salt (as such or in form of a cosmetic preparation) of the present disclosure which is effective for producing the desired effect of hair repair.

Typically, the pH of the cosmetic preparation is 3.5-6, particularly 4-5 at 20° C. The pH may, for example, be adjusted using lactic acid, citric acid and the like.

Typically, the concentration of the salt disclosed herein will be between 0.01% and 5% by weight of the cosmetic preparation, such as 2%-4% by weight. In some embodiments, the concentration of the salt disclosed herein is 50-130 mmol per liter of the cosmetic preparation, particularly 80-100 mmol per liter.

In some embodiments, the cosmetic preparation comprises a solubilizer. The concentration of the solubilizer may, for example, be 5%-20% by weight of the cosmetic preparation, particularly 10%-20%, e.g. 15%-20%.

In some embodiments, the cosmetic preparation comprises phenoxyethanol at a concentration of 0.1%-1.7% by weight of the cosmetic preparation, particularly 0.7%-1.1%, e.g. 0.9%.

In some embodiments, the cosmetic preparation comprises ethylhexylglycerin at a concentration of 0.01%-0.2% by weight of the cosmetic preparation, particularly 0.08%-0.12%, e.g. 0.1%.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject salt or compound from one organ, or portion of the body, to another organ, or portion of the body. Each carrier must be "acceptable" in the sense of being compatible with the other ingredients of the formulation and not injurious to the person being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in cosmetic preparations.

Such compositions may contain further components conventional in cosmetic preparations, e.g. wetting agents, emulsifiers and lubricants, such as sodium lauryl sulfate and magnesium stearate, as well as coloring agents, release agents, coating agents, sweetening, flavoring and perfuming agents, preservatives and antioxidants, pH modifiers, bulking agents, and further active agents. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Such compositions may be prepared by any method known in the art, for example, by bringing into association the active ingredient with one or more carriers and/or excipients. Different compositions and examples of carriers and/or excipients are well known to the skilled person and are described in detail in, e.g., Remington: The Science and Practice of Pharmacy. Pharmaceutical Press, 2013; Rowe, Sheskey, Quinn: Handbook of Pharmaceutical Excipients. Pharmaceutical Press, 2009. Excipients that may be used in the preparation of the cosmetic preparations may include one or more of buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide a composition or preparation suitable for an administration of choice.

The cosmetic preparations of the disclosure may be in any suitable form. In some embodiments, such suitable forms include but are not limited to liquids, e.g. low to moderate viscosity liquids, such as lotions, milks, mousses, sprays, gels, creams, ointments, pastes and the like. Suitable excipients, such as those listed above, are included or excluded from the skin formulation depending on the form of use of the formulation (e.g., lotion, gel, ointment, or cream).

Liquid forms of the salts of the disclosure include pharmaceutically acceptable emulsions, microemulsions, solutions, suspensions, syrups and elixirs. In addition to the active ingredient, the liquid forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. In form of suspensions, a salt may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In form of sprays, ointments, pastes, creams, lotions, gels, solutions, a salt or compound may be mixed under sterile conditions with a pharmaceutically-acceptable carrier, and with any preservatives, buffers, or propellants which may be required. Such ointments, pastes, creams and gels may contain, in addition to a salt of the disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In form of powders and sprays, a salt of the disclosure, may contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

In some embodiments, the cosmetic preparations are hair care products, which includes products in form of a shampoo, a conditioner, a hair mask, a hair rinse, hair spray, hair foam, hair mousse, hair gel, hair tonic, and the like.

It is understood that all contemplated compositions and preparations must be stable under the conditions of manufacture and storage, and preserved against the contaminating action of microorganisms, such as bacteria and fungi.

The amounts of a salt of the disclosure in the cosmetic preparations of the disclosure may be adjusted in order to obtain an amount of a salt of the disclosure which is effective to achieve the desired cosmetic response for a particular person, composition, and mode of administration, without being deleterious to the person. The chosen amount will depend upon a variety of factors including the nature of the particular salt of the present disclosure used, the route of administration, the time of administration, the duration of the treatment, other compounds, salts and/or materials used in combination with the particular salt, the age, sex, weight, condition, general health and prior medical history of the person being treated, and like factors well known in the medical arts.

Typically, a suitable amount of a salt of the disclosure will be that amount of the salt, which is the lowest amount effective to produce a desired effect. Such an effective dose will generally depend upon the factors described above. In form of shampoo, the amount of cosmetic preparation applied per treatment may, for example, be 1 g-10 g. In form of conditioner and/or hair mask, the amount of cosmetic preparation applied per treatment may, for example, be 1 g-10 g. In form of leave-on conditioner or leave-on mask, the amount of cosmetic preparation applied per treatment may, for example, be 0.1 g-7 g.

All of the salts, compositions, preparations and/or methods disclosed and claimed herein can be made and executed without undue experimentation in light of the present disclosure. It will be apparent to those of skill in the art that variations may be applied to the present disclosure without departing from the scope of the disclosure. The Examples provided herein are intended to be illustrative and are not exhaustive; thus, the illustrated Examples should not be viewed as limiting the disclosure in any way.

EXAMPLES

Materials:

N-Cbz-cysteine was obtained by reduction of its cysteine counterpart via a literature known method. *Adv. Syn. Catal.*, 2020, 362, 5093-5104. DOI: 10.1002/adsc.202000716. "OLAPLEX® N° 0 Intensive Bond Building Hair Treatment" is a commercially available product which comprises an active agent, water, phenoxyethanol and sodium benzoate. The active agent is hereinafter labelled "Olaplex active agent".

Example 1: Synthesis of Olaplex Active Agent

The active agent "Olaplex active agent", which was used as a reference compound in example 8, has the following structure:

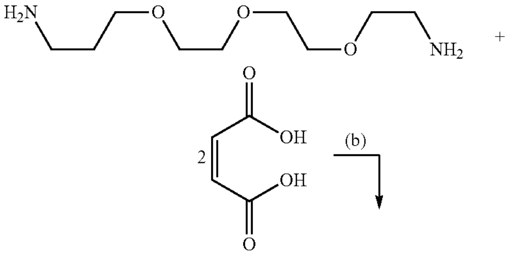

-continued

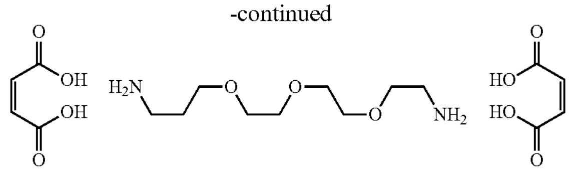

Olaplex active agent

It was synthesized by reacting 2 equivalents of the corresponding acid with 1 equivalent of the corresponding diamine.

Example 2: Synthesis of Salt 15 (SPC-TB-0015)

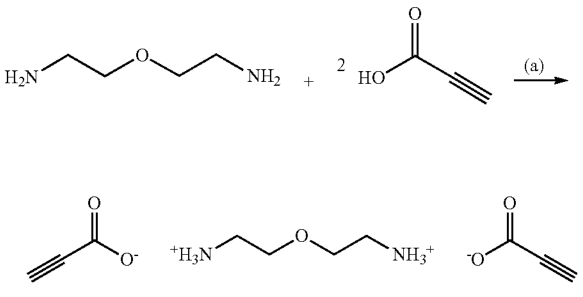

SPC-TB-0015

(a) SPC-TB-0015

To a solution of 2,2'-oxybis(ethan-1-amine) (100 mg, 1.0 eq, 0.96 mmol) in DCM (1.92 mL) was added propiolic acid (134 mg, 2.0 eq., 1.92 mmol). After 2 h of reaction time the solvent was concentrated to receive the resulting salt as orange oil (235 mg, quant.).

$^1H$ NMR (400 MHz, DMSO) δ 8.29 (m, 6H), 3.59 (dd, J=5.6 Hz, 4.4 Hz, 4H), 3.16 (m, 2H), 2.97 (dd, J=5.6 Hz, 4.4 Hz, 4H).

Example 3: Synthesis of Salt 16 (SPC-TB-0016)

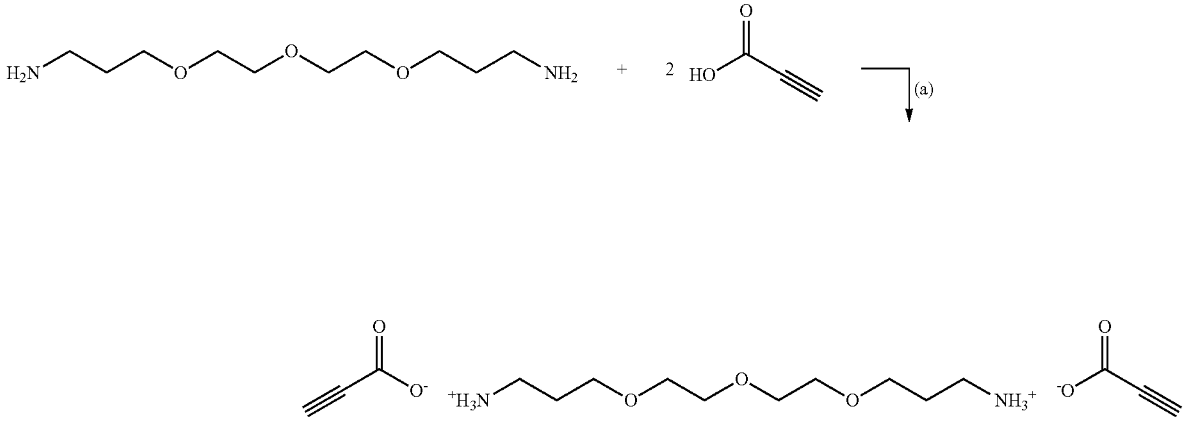

SPC-TB-0016

(a) SPC-TB-0016

To a solution of 3,3'-((oxybis(ethane-2,1-diyl))bis(oxy))bis(propan-1-amine) (500 mg, 1.0 eq, 2.27 mmol) in DCM (4.54 mL) was added propiolic acid (318 mg, 2.0 eq., 4.53 mmol). After 2 h of reaction time the solvent was concentrated to receive the resulting salt as an orange oil (818 mg, quant.).

$^1H$ NMR (400 MHz, DMSO) δ 8.08 (s, 6H), 3.55-3.42 (m, 12H), 2.99 (s, 2H), 2.87-2.76 (m, 4H), 1.78 (p, J=8.0, 6.2 Hz, 4H).

Example 4: Synthesis of Salt 17 (SPC-TB-0017)

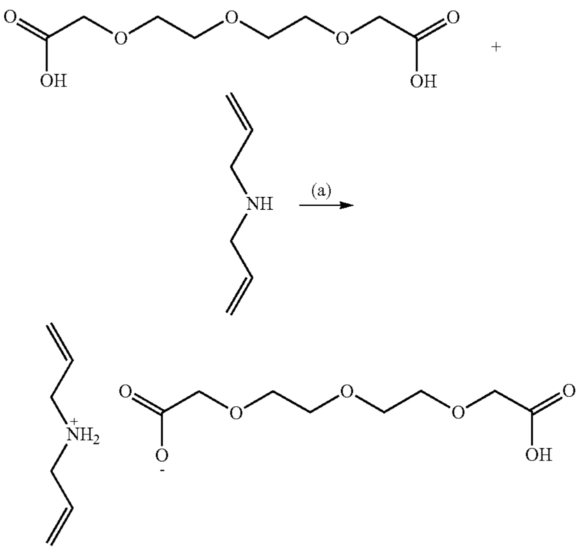

SPC-TB-0017

Example 5: Synthesis of Salt 18 (SPC-TB-0018)

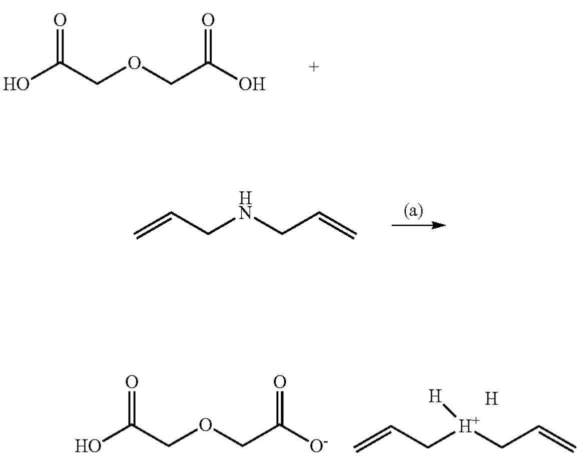

SPC-TB-0018

(a) SPC-TB-0018

On 15 g scale, the procedure was modified:

2,2'-oxydiacetic acid (15.0 g, 1 Eq, 112 mmol) was suspended in MeCN (122 mL) at rt. Then diallylamine (10.9 g, 13.8 mL, 1 Eq, 112 mmol) was added dropwise (at which point everything dissolves) and the solution was stirred at room temperature for 1 h. The solvent was concentrated to obtain the resulting salt as an off-white solid (25.9 g, quant.).

$^1H$ NMR (400 MHz, DMSO) δ 5.35 (m, 2H), 5.40 (m, 4H), 3.93 (s, 4H), 3.53 (d, J=2.7 Hz, 4H).

Example 6: Synthesis of Salt 19 (SPC-TB-0019)

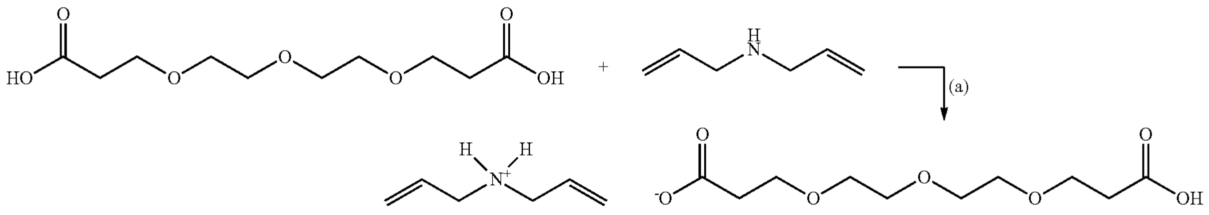

SPC-TB-0019

(a) SPC-TB-0017

To a solution of 2,2'-((oxybis(ethane-2,1-diyl))bis(oxy))diacetic acid (5.000 g, 1 Eq, 22.50 mmol) dissolved in MeCN (24.46 ml) was added diallylamine (2.186 g, 2.78 mL, 1 Eq, 22.50 mmol) slowly at rt. The solution is stirred at rt for 2 h. The solvent was removed under reduced pressure to afford the resulting salt (7.179 g, 22.48 mmol, 99.90%) as a yellow oil.

$^1H$ NMR (400 MHz, DMSO) δ 9.03 (s, 2H), 5.87 (ddt, J=16.8, 10.4, 6.3 Hz, 2H), 5.35-5.17 (m, 4H), 3.88 (s, J=1.5 Hz, 4H), 3.54 (dddt, J=7.8, 5.8, 4.2, 2.1 Hz, 8H), 3.30 (d, J=20.1 Hz, 5H).

(a) SPC-TB-0019

To a solution of 3,3'-((oxybis(ethane-2,1-diyl))bis(oxy))dipropionic acid (400 mg, 1.0 eq, 1.60 mmol) in DCM (16.0 mL) was added diallylamine (311 mg, 2.0 eq., 3.20 mmol). After 2 h of reaction time the solvent was concentrated to obtain the resulting salt as colorless oil (580 mg, quant.).

$^1H$ NMR (400 MHz, DMSO) δ 5.82 (m, 2H), 5.12 (m, 4H), 3.59 (t, J=6.4 Hz, 4H), 3.15 (m, 4H), 2.42 (t, J=6.4 Hz, 4H).

Example 7: Synthesis of Salt 20 (SPC-TB-0020)

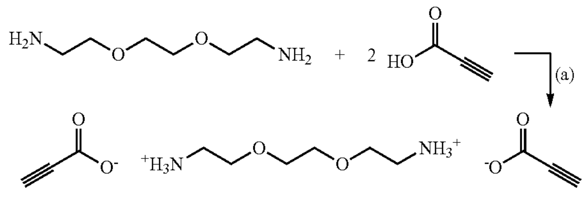

SPC-TB-0020

(a) SPC-TB-0020

To a solution of 2,2'-(ethane-1,2-diylbis(oxy))bis(ethan-1-amine) (5.00 g, 1.00 Eq, 34.0 mmol) in DCM (14.0 mL) at 0° C. was added propiolic acid (4.20 mL, 2.00 Eq, 67.0 mmol) in DCM (14.0 mL) precooled to 0° C. Caution: very exothermic reaction, add very slowly. The reaction mixture was stirred at 0° C. for 15 min and allowed to warm to rt for 1 h. It was concentrated under reduced pressure to produce an orange oil (quant yield).

$^1$H NMR (400 MHz, DMSO) δ 3.63-3.56 (m, 8H), 3.04 (s, 2H), 2.95 (t, J=5.4 Hz, 4H).

Example 8: Thiol Recombination

General Procedure

The compound to be tested (1 eq.) was dissolved in an aqueous media (0.02 M) and 4 eq. of cysteine reagent (N-Cbz-cysteine) were added. A phosphate buffer (pH=5.4) was used as aqueous medium.

To make the phosphate buffer a solution of 0.1-M solution of citric acid (use citric acid monohydrate) and a 0.2-M solution of $Na_2HPO_4$ (use $Na_2HPO_4$ or $Na_2HPO_4$*$2H_2O$) were prepared and mixed with the following ratio: 44.25 mL/55.75 mL=mL 0.1M-citric acid/mL 0.2M $Na_2HPO_4$ to give a buffer solution with pH=5.4.

The tests were performed at ambient temperature of 30° C. under stirring with small magnetic stirrers in LC-MS vials or small glass vials. The reactions were performed under normal atmosphere. The reactions were monitored by LC-MS. The reaction scale was between 4 and 10 mg of tested compound. To calculate the conversion into products the ratio between cysteine reagent, the respective mono-adduct (mono) and bis-adduct (bis) as shown in the following schemes were compared.

The tested compounds show improved reactivity with the cysteine derivative compared to the Olaplex active agent.

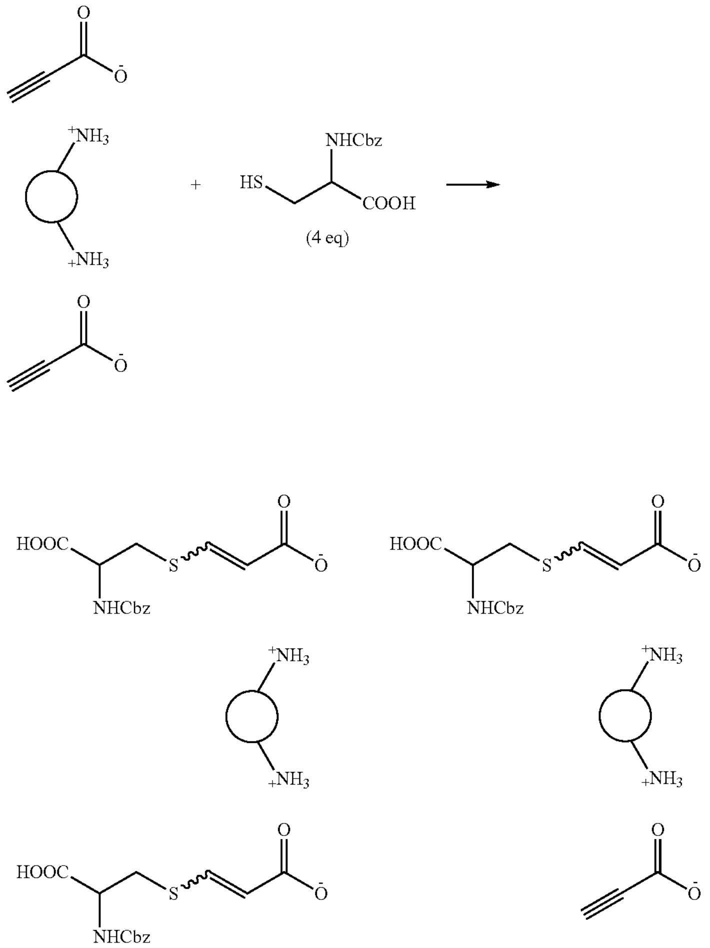

bis mono

-continued

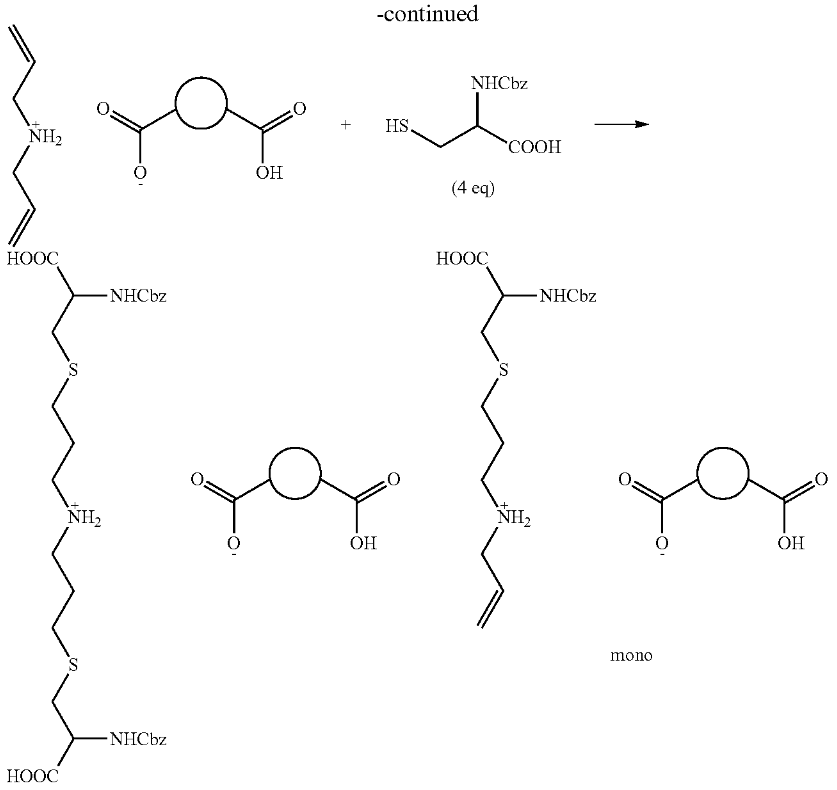

mono bis

Results

| Test compound | Conversion at 30 min | Conversion at 60 min | Conversion at 5 h |
|---|---|---|---|
| Olaplex active agent | 4% bis | 7% bis | 18% bis |
| SPC-TB-0015* | — | 12% bis | — |
| SPC-TB-0018* | — | 15% bis | — |

*conversion was assessed after dilution of the reaction mixture with MeCN.

The invention claimed is:

1. A salt of formula I $$[G]_g^q\ [A—L—E]^p \qquad \text{I}$$

wherein q is + or −;

p is 2+, +, − or 2−;

g is 1 or 2;

G is selected from $R^5$—C≡C—$CO_2^-$, $R^5$—C≡C—C(═O)$S^-$, $R^5$—C≡C—$CS_2^-$, $R^5$—C≡C—$SO_2^-$; $R^5$—C≡C—S(═O)$S^-$, $R^5$—C≡C—$SO_3^-$, $R^5$—C≡C—S(═O)$_2S^-$, and a diallylammonium group, wherein $R^5$ is independently selected from H, linear or branched $C_{1-6}$ alkyl;

L is straight-chain $C_{1-15}$ alkyl, wherein one or more $CH_2$ groups are independently replaced by —($CH_2$—O—$CH_2$)—, —($CH_2$—$CH_2$—O)—, —(O—$CH_2$—$CH_2$)—, C═O, —O—, —S—, —NH— or —$NR^1$—, wherein $R^1$ is linear or branched $C_{1-6}$ alkyl;

A is selected from $NR^2_3{}^+$, $CO_2^-$, C(═O)$S^-$, $CS_2^-$, $SO_2^-$, S(═O)$S^-$, $SO_3^-$ and S(═O)$_2S^-$, wherein $R^2$ is, for each occurrence independently, selected from H, linear or branched $C_{1-6}$ alkyl;

E is selected from $NR^3_2$, $NR^3_3{}^+$, $CO_2H$, C(═O)SH, $CS_2H$, $SO_2H$, S(═O)SH, $SO_3H$, S(═O)$_2$SH, $CO_2^-$, C(═O)$S^-$, $CS_2^-$, $SO_2^-$, S(═O)$S^-$, $SO_3^-$, S(═O)$_2S^-$, wherein, for each occurrence independently, $R^3$ is selected from H, linear or branched $C_{1-6}$ alkyl;

wherein the overall charge of A and E is not 0 and the salt of formula I is overall neutral in charge, and wherein the values of q and p represent the overall charge within the preceding bracket.

2. A salt according to claim 1 having formula II

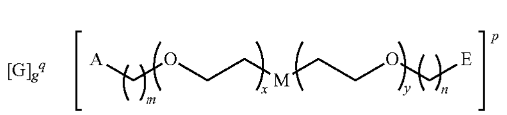

II wherein q is + or −;

p is 2+, +, − or 2−;

g is 1 or 2;

G is selected from $R^5$—C≡C—$CO_2^-$, $R^5$—C≡C—C(═O)$S^-$, $R^5$—C≡C—$CS_2^-$, $R^5$—C≡C—$SO_2^-$, $R^5$—C≡C—S(═O)$S^-$, $R^5$—C≡C—$SO_3^-$, $R^5$—C≡C—S(═O)$_2S^-$, wherein $R^5$ is independently selected from H, linear or branched $C_{1-6}$ alkyl, and $(CH_2═CH—CH_2)_iNR^4_{(4-i)}{}^+$, wherein i is independently selected from 2 and 3, wherein $R^4$ is independently selected from H, linear or branched $C_{1-6}$ alkyl;

A is selected from $NR^2_3{}^+$, $CO_2^-$, $C(=O)S^-$, $CS_2^-$, $SO_2^-$, $S(=O)S^-$, $SO_3^-$, $S(=O)_2S^-$, wherein $R^2$ is, for each occurrence independently, selected from H, linear or branched $C_{1-6}$ alkyl;

E is selected from $NR^3_2$, $NR^3_3{}^+$, $CO_2H$, $C(=O)SH$, $CS_2H$, $SO_2H$, $S(=O)SH$, $SO_3H$, $S(=O)_2SH$, $CO_2^-$, $C(=O)S^-$, $CS_2^-$, $SO_2^-$, $S(=O)S^-$, $SO_3^-$, $S(=O)_2S^-$, wherein, for each occurrence independently, $R^3$ is selected from H, linear or branched $C_{1-6}$ alkyl;

M is selected from O, S, NH and $NR^1$, wherein $R^1$ is linear or branched $C_{1-6}$ alkyl;

m and n are independently selected from 1, 2 and 3;

x and y are independently selected from 0, 1 and 2;

wherein the overall charge of A and B is not 0 and the salt of formula I is overall neutral in charge.

3. A salt according to claim 1, wherein the diallylammonium group is a moiety of formula d1 or d2 d1

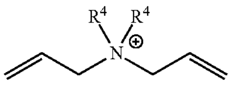

d2

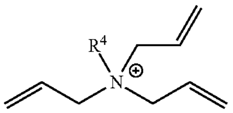

wherein, for each occurrence independently, $R^4$ is selected from H, linear or branched $C_{1-6}$ alkyl.

4. A salt according to claim 1 having formula III

III

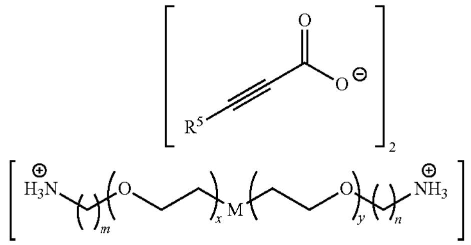

wherein

M is selected from O, S and $NR^6$, wherein $R^6$ is selected from H, linear or branched $C_{1-6}$ alkyl;

$R^5$ is, for each occurrence independently, selected from H, linear or branched $C_{1-6}$ alkyl;

m and n are independently selected from 1, 2 and 3;

x and y are independently selected from 0, 1 and 2.

5. A salt according to claim 4, wherein $R^5$ is H and M is O.

6. A salt according to claim 4, wherein m and n are independently selected from 2 or 3.

7. A salt according to claim 1 having formula IV

IV

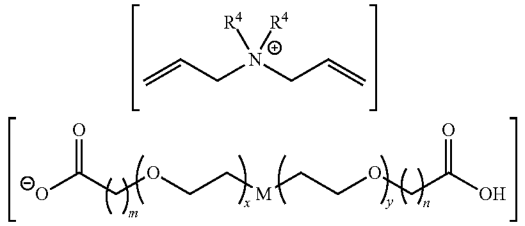

wherein

M is selected from O, S and $NR^6$, wherein $R^6$ is selected from H, linear or branched $C_{1-6}$ alkyl;

$R^4$ is, for each occurrence independently, selected from H, linear or branched $C_{1-6}$ alkyl;

m and n are independently selected from 1, 2 and 3;

x and y are independently selected from 0, 1 and 2.

8. A salt according to claim 7, wherein $R^4$ is H and M is O.

9. A salt according to claim 7, wherein m and n are independently selected from 1 and 2.

10. A salt according to claim 2, wherein m is equal to n and, optionally, x is equal to y.

11. Cosmetic preparations comprising at least one salt according to claim 1.

12. Cosmetic preparations according to claim 11 further comprising at least one cosmetic additive selected from the group consisting of surfactants, oil components, emulsifiers, pearlescent waxes, consistency-enhancing agents, thickeners, superfatting agents, stabilizers, polymers, silicone compounds, fats, waxes, lecithins, phospholipids, UV light protection factors, humectants, biogenic agents, antioxidants, deodorants, antiperspirants, antidandruff agents, film-forming agents, swelling agents, insect repellents, self-tanning agents, tyrosine inhibitors (depigmentation agents), hydrotropes, solubilizers, preservatives, perfumed oils and dyes, as well as mixtures thereof.

13. Cosmetic preparations according to claim 11 further comprising a carrier.

14. A method of using the salts according to claim 1 for the production of cosmetic preparations and hair care products.

15. A method for treatment of keratin materials, such as hair, the method comprising applying to the keratin materials a salt according to claim 1.

16. A salt according to claim 6, wherein m and n are both selected from 2 or 3.

17. Cosmetic preparations according to claim 13 wherein the carrier is selected from water, C(2-6)-alcohols, C(1-10) polyols, or oil components.

* * * * *